United States Patent
Son et al.

(10) Patent No.: US 7,192,591 B2
(45) Date of Patent: Mar. 20, 2007

(54) **PHARMACEUTICAL COMPOSITION COMPRISING AN EXTRACT OF *ELFVINGIA APPLANATA* FOR THE PREVENTION AND THE TREATMENT OF DIABETES AND DIABETIC COMPLICATIONS**

(76) Inventors: Dal-Hoon Son, #7933, Mount Carmel BLVD., Niagara Falls, Ontario (CA) L2H 2Y1; Sung-Soon Son, #7933, Mount Carmel BLVD., Niagara Falls, Seoul (CA) L2H 2Y1; Kuk-Hyun Shin, 13-908 Eunma APT. 316, Daechi 2-dong, Kangnam-gu, Seoul (KR) 135-778; Sam-Sik Kang, 201, City-3 cha APT. 105, Cheongdam 1-dong, Kangnam-gu, Daejeon (KR) 135-956

( * ) Notice: Subject to any disclaimer, the term of this patent is extended or adjusted under 35 U.S.C. 154(b) by 0 days.

(21) Appl. No.: 11/067,128

(22) Filed: Feb. 25, 2005

(65) Prior Publication Data

US 2005/0142147 A1 Jun. 30, 2005

Related U.S. Application Data

(63) Continuation of application No. PCT/KR02/01635, filed on Aug. 30, 2002, now abandoned.

(51) Int. Cl.
*A61K 35/84* (2006.01)

(52) U.S. Cl. .................................... 424/195.15
(58) Field of Classification Search .............. None
See application file for complete search history.

(56) References Cited

U.S. PATENT DOCUMENTS

| 5,603,937 | A | * | 2/1997 | Kondoh et al. | ........ 424/195.15 |
| 6,841,180 | B2 | * | 1/2005 | Kim et al. | .............. 426/7 |
| 2002/0192334 | A1 | * | 12/2002 | Kim et al. | ............. 426/52 |

FOREIGN PATENT DOCUMENTS

| JP | 62022723 | * | 1/1987 |
| JP | 07000116 | * | 1/1995 |

OTHER PUBLICATIONS

Kim et al. Yakhak Hoechi. 1994. vol. 38, No. 6, pp. 742-748, CAPLUS Abstract enclosed.*

* cited by examiner

*Primary Examiner*—Christopher R. Tate
(74) *Attorney, Agent, or Firm*—Anderson Kill & Olick, PC

(57) ABSTRACT

The present invention relates to an extract of *Elfvingia applanata*, which shows a therapeutic activity for diabetes and diabetic complications and a pharmaceutical composition for the treatment of diabetes and diabetic complications comprising the extract.

2 Claims, 4 Drawing Sheets

PHARMACEUTICAL COMPOSITION COMPRISING AN EXTRACT OF *ELFVINGIA APPLANATA* FOR THE PREVENTION AND THE TREATMENT OF DIABETES AND DIABETIC COMPLICATIONS

CROSS REFERENCE TO RELATED APPLICATION

This application is a continuation patent application of PCT Patent Application No. PCT/KR2002/001635, which was filed on Aug. 30, 2002, designating the United States of America, now abandoned.

DESCRIPTION

1. Field of the Invention

The present invention relates to a pharmaceutical composition comprising an extract of *Elfvingia applanata* for the prevention and the treatment of diabetes and diabetic complications, and the use thereof.

2. Background of the Invention

Diabetes mellitus is a mammalian condition in which the amount of glucose in the blood plasma is abnormally high. Elevated glucose levels in some instances can lead to higher than normal amounts of particular hemoglobin, HbA1c. This condition can be life-threatening and high glucose levels in the blood plasma, hyperglycemia, can lead to a number of chronic diabetes syndromes, for example, atherosclerosis, microangiopathy, kidney disorders or failure, cardiac disease, diabetic retinopathy and other ocular disorders, including blindness.

Diabetes mellitus is known for two forms of the disease. In the form of this disease known as Type II, non-insulin dependent diabetes (NIDDM) or adult-onset, as opposed to juvenile diabetes or Type I, the pancreas often continues to secrete normal amounts of insulin. However, this insulin is ineffective in preventing the symptoms of diabetes which include cardiovascular risk factors such as hyperglycemia, impaired carbohydrate mechanism, particularly glucose metabolism, glycosuria, decreased insulin sensitivity, centralized obesity hypertriglyceridemia, low HDL levels, elevated blood pressure and various cardiovascular effects attending these risk factors. Many of these cardiovascular risk factors are known to precede the onset of diabetes by as much as a decade. These symptoms, if left untreated, often lead to severe complications, including premature atherosclerosis, retinopathy, nephropathy, and neuropathy. Insulin resistance is believed to be a precursor to overt NIDDM and strategies directed toward ameliorating insulin resistance may provide unique benefits to patients with NIDDM.

Current drugs used for managing Type II diabetes and its precursor syndromes, such as insulin resistance, fall within five classes of compounds: the biguanides, thiazolidinediones, the sulfonylureas, benzoic acid derivatives and alpha-glucosidase inhibitors. The biguanides, such as metformin, are believed to prevent excessive hepatic gluconeogenesis. The thiazolidinediones are believed to act by increasing the rate of peripheral glucose disposal. The sulfonylureas, such as tolbutamide and glyburide, the benzoic acid derivatives, such as repaglinide, and the alpha-glucosidase inhibitors, such as acarbose, lower plasma glucose primarily by stimulating insulin secretion.

Above sulfonylureas have disadvantages that these drugs cannot be administered to IDDM patient, NIDDM patient having decreased insulin secretion, and fecund female being worried about anomalous child birth, abortion and stillbirth. Additionally, most of the sulfonylureas should be administered carefully to liver dysfunction patient and kidney dysfunction patient because of sulfonylurea metabolism.

The pathway of biguanides such as metformin has not been verified clearly but the biguanides cannot increase the insulin secretion of pancreas. The biguanides have lower glucose-decreasing effect than the sulfonylureas but have low occurrence of hypoglycemia. And the biguanides treatment may happen nausea, vomiting, diarrhea, eruption etc. in early stage and causes lactic acidosis of fatal side effect, so those are used only as experimental agents in U.S.A.

The sulfonylureas or the biguanides have above disadvantages and side effects; therefore it is required to develop a new hypoglycemic drug having fewer side effects and greater safeties for effective treatment than those of current drugs.

SUMMARY OF THE INVENTION

Accordingly, it is an object of the present invention to provide an extract of *Elfvingia applanata*, which has an activity of decreasing glucose level, inhibiting aldose reductase and decreasing sorbitol.

It is another object of the present invention to provide a process for preparing above extract to treat diabetes and diabetic complications.

It is another object of the present invention to provide a pharmaceutical composition comprising the above extract and a pharmaceutically acceptable carrier for the prevention and treatment of diabetes and diabetic complications without creating side effects.

It is another object of the present invention to provide a use of above extract for the preparation of pharmaceutical composition to treat diabetes and diabetic complications.

It is another object of the present invention to provide a health care food comprising above extract and a sitologically acceptable additive to prevent and treat diabetes and diabetic complications.

BRIEF DESCRIPTION OF THE DRAWINGS

The above and other objects, features and other advantages of the present invention will more clearly understood from the following detailed description taken in conjunction with the accompanying drawings, in which.

DETAILED DESCRIPTION OF THE INVENTION

Figure 1:
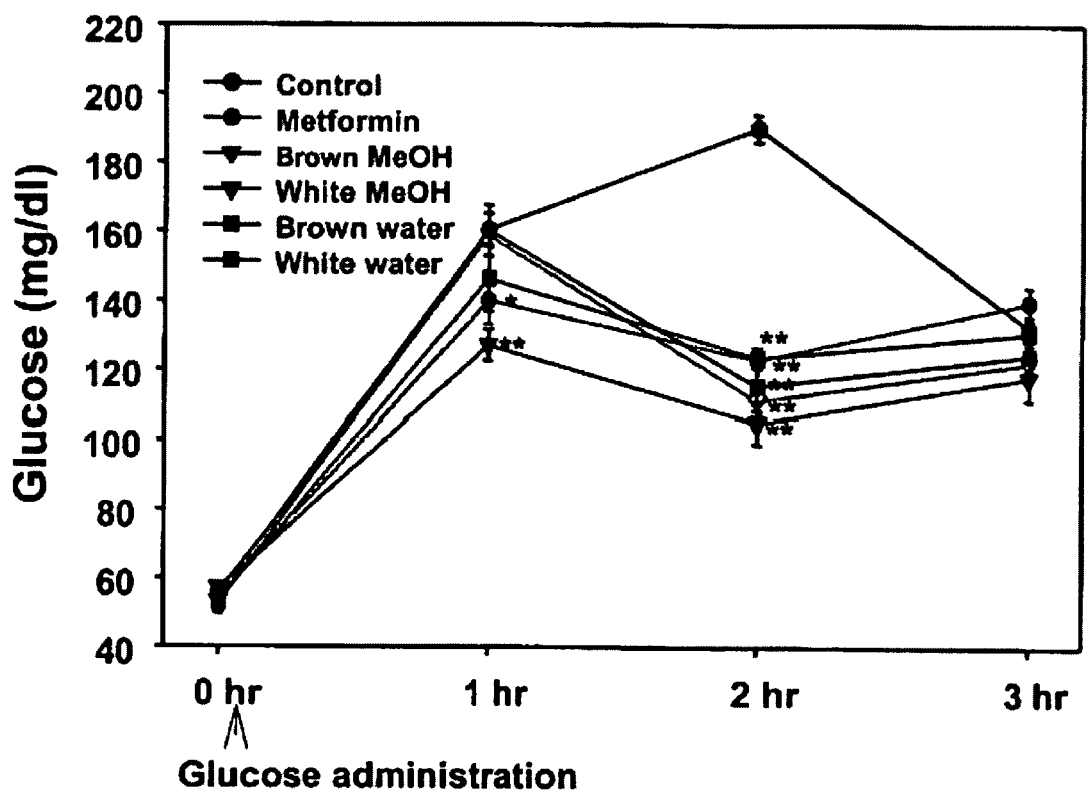
FIG. 1 depicts the effect of *Elfvingia applanata* on oral glucose tolerance in normal rats.

In accordance with on aspect of the present invention, there are provided an extract of *Elfvingia applanata*, which shows an effective therapeutic activity against diabetes and diabetic complications, and a pharmaceutical composition for the treatment of diabetes and diabetic complications, which comprises the extract and a pharmaceutically acceptable carrier.

In accordance with the present invention, it has been found that an extract of *Elfvingia applanata* possesses the ability to decrease the glucose level of blood and to prevent diabetes complications by inhibiting sorbitol increase.

*Elfvingia applanata* KARST employed in the present invention is belong to Polyporaceae and is distributed all over the world. *Elfvingia applanata* KARST, white rot mycelium, grows naturally on a latifoliate tree horizontally in summer and its fruit body is an annual plant in the form of semicircle and is known to have anti-cancer effect.

An inventive extract may be prepared in accordance with the following preferred embodiment.

*Elfvingia applanata* is divided into brown and white parts and pulverized. The each powder is mixed with 1 to 10-fold, preferably, 5-fold volume of water, lower alcohols such as methanol, ethanol and the like, or the mixtures thereof; and is heated at a temperature ranging from 60 to 90° C., preferably 80° C., for a period ranging from 1 to 24 hours, preferably 5 hours, with 3 to 10 times, preferably 7 times, to obtain an aqueous crude extract. The crude extract is centrifuged, filtered and then lyophilized to obtain an extract powder. The powder is stored at 4° C. until use.

The extract of the present invention exhibits a high level of ability to inhibit increasing of blood glucose level.

Further, the extract of the present invention inhibit the increase of sorbitol level, which may cause diabetic complications such as neuropathy, retinopathy, cataract, nephropathy and the like.

As described above, the extract of *Elfvingia applanata* KARST can be used as an effective pharmaceutical agent for the treatment of diabetes, which has little toxicity and causes no adverse effect.

Accordingly, the present invention also provides a pharmaceutical composition for treatment of diabetes, which comprises the extract of *Elfvingia applanata* KARST as an active ingredient, in combination with pharmaceutically acceptable excipients, carriers or diluents.

A pharmaceutical formulation may be prepared by using the composition in accordance with any of the conventional procedures. In preparing the formulation, the active ingredient is preferably admixed or diluted with a carrier or enclosed within a carrier, which may be in the form of a capsule, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, mannitol, starches, gum acacia, alginates, gelatin, calcium phosphate, calcium silicate, cellulose, methylcellulose, microcrystalline cellulose, polyvinylpyrrolidone, water, methylhydroxybenzoates, propylhydroxybenzoates, talc, magnesium stearate and mineral oil.

The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

The pharmaceutical formulations can be administered via various routes including oral, transdermal, subcutaneous, intravenous and intramuscular introduction. A typical daily dose of the active ingredient may range from about 20 to 100 mg/kg body weight, preferably 40 to 80 mg/kg body weight, and can be administered in a single dose or in divided dose. However, it should be understood that the amount of the active ingredient actually administered ought to be determined in light of various relevant factors including the condition to be treated, the chosen route of administration, the age, sex and body weight of the individual patient, and the severity of the patient's symptom; and. Therefore, the above dose should not be intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

Accordingly, the present invention also provides a health care food for the prevention of diabetes, which comprises the extract of *Elfvingia applanata* KARST as an active ingredient, in combination with sitologically acceptable additive.

Above described the extract of *Elfvingia applanata* KARST therein can be added to food or beverage for prevention of diabetes and diabetic complications. For the purpose of preventing diabetes and diabetic complications, wherein, the amount of above described extract in food or beverage may generally range from about 0.1 to 15 w/w %, preferably 1 to 10 w/w % of total weight of food for the health food composition and 1 to 30 g, preferably 3 to 10 g on the ratio of 100 ml of the health beverage composition.

Providing that the health beverage composition of present invention contains above described extract as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition.

Examples of addable food comprising aforementioned extract therein are various food, beverage, gum, vitamin complex and health improving food et al.

BEST MODE FOR CARRING OUT THE INVENTION

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Reference Example, Examples and Experimental Examples are intended to further illustrate the present invention without limiting its scope.

Example 1

Preparation of the Methanol Extract of *Elfvingia applanata*

Brown part and white part of *Elfvingia applanata* were separated, dried and pulverized. Each 300 g of white and brown part of *Elfvingia applanata* was extracted seven times with 1.5 L of methanol, respectively, for 5 hours under reflux. The resulting extracts were combined and concentrated under reduced pressure to afford 15.6 g of brown part extract (sample 1) and 11.7 g of white part extract (sample 2), respectively.

Example 2

Preparation of the Water Extract of *Elfvingia applanata*

Brown part and white part of *Elfvingia applanata* were separated, dried and pulverized. Each 300 g of white and brown part of *Elfvingia applanata* was extracted four times with 1.5 L of distilled water, respectively, for 5 hours under reflux. The resulting extracts were combined, concentrated under reduced pressure and lyophilized to afford 14.1 g of brown part (sample 3) and 17.4 g of white part (sample 4), respectively.

Experimental Example 1

Effect of *Elfvingia applanata* Extracts on Blood Glucose Level

Preparation of Diabetes-Induced SD Rats

All experiments were performed on Sprague-Dawley (SD) rats aged 10 weeks, weighed 200–250 g and purchased from the Seoul national university. The animals were acclimatized for 1–2 weeks before being used for the experiments. Standard pelleted diet and water were given ad libitum. Animals were maintained under constant 12 hours light and dark cycle and an environmental temperature ranging from 21 to 23° C.

Diabetes mellitus was induced in male SD rats, weighing 220–250 g, by a single intraperitoneal injection of strptozotocin (Sigma chemical CO., St. Louis, Mo., USA) dissolved in phosphate buffered saline acidified to pH 4.5 with 0.05 M citric acid (66 mg/kg body wt). Control rats were injected with the vehicle only. The animals were fed standard Lab. Chows and water ad. Lib. throughout the experiments. Two weeks later, the diabetes-induced rats were used in following experiments.

Among diabetes-induced rats prepared by the procedure described above, the SD rats showing higher serum glucose level than 600 mg/dl were selected, then epalrestat and *Elfvingia applanata* extracts were administered via an intragastric tube, once a day at a dose of 200 mg/kg/day for 2 weeks. Epalrestat is a kind of diabetes therapeutics having the inhibitory activity of aldose reductase known in the art. *Elfvingia applanata* extracts were suspended in saline containing 0.5% carboxymethyl cellulose. The animals were then sacrificed under ether anesthesia and their blood samples were collected. Plasma glucose levels were determined by using a commercial kit.

TABLE 1

The effect of *Elfvingia applanata* extracts on plasma glucose content in STZ-diabetic rats.

| Sample | Plasma glucose (g/l) | Inhibition (%) |
|---|---|---|
| Normal | 1.2 ± 0.1 | — |
| Control | 5.7 ± 0.3 | — |
| Epalrestat | 3.9 ± 0.2** | 31.6 |
| Sample 1 | 3.8 ± 0.3** | 33.3 |
| Sample 2 | 3.4 ± 0.4** | 40.4 |
| Sample 3 | 4.5 ± 0.5 | 21.1 |
| Sample 4 | 4.8 ± 0.3* | 15.8 |

Significantly different from the control:
**$p < 0.01$,
*$p < 0.05$.

As can be seen in Table 1, inventive extracts-administered groups showed the significant decrease in plasma glucose level comparing with that of control group. And the methanol extracts from brown and white part showed the similar hypoglycemic effect to that of epalrestat.

Experimental Example 2

Effect of *Elfvingia applanata* Extracts on Glucose Tolerance in SD Rats

Prior to an oral glucose tolerance test, rats were fasted for 16 hours. And then saline for control group, 250 mg/kg of metformin, one of the biguanides drug for comparison group and each 300 mg/kg of *Elfvingia applanata* extracts, respectively, was orally administered to each group consisting of 10 rats. Thirty minutes later, 3 g/kg of glucose was orally administered to each rat with a feeding syringe. Blood samples were collected from carotid artery at (just before the oral administration of glucose), 60, 120, and 180 mins after glucose load for glucose assay.

TABLE 2

Effect of *Elfvingia applanata* extracts on glucose tolerance.

| | Glucose (mg/dl) | | | |
|---|---|---|---|---|
| Samples | 0 hr | 1 hr | 2hr | 3hr |
| Control | 55.5 ± 1.9 | 160.3 ± 4.8 | 189.7 ± 4.0 | 132.1 ± 3.4 |
| Metformin | 54.5 ± 2.2 | 140.1 ± 7.0* | 122.8 ± 1.4** | 139.7 ± 4.5 |
| Sample 1 | 53.3 ± 3.6 | 158.9 ± 0.8 | 111.0 ± 4.3** | 121.9 ± 5.3 |
| Sample 2 | 57.2 ± 0.5 | 127.1 ± 4.6** | 104.8 ± 6.0** | 117.9 ± 6.7 |
| Sample 3 | 53.9 ± 2.5 | 146.5 ± 9.7 | 123.4 ± 2.9** | 130.5 ± 3.3 |
| Sample 4 | 52.7 ± 3.0 | 160.2 ± 7.4 | 115.2 ± 7.2** | 124.3 ± 4.4 |

Significantly different from the control:
**$p < 0.01$,
*$p < 0.05$.

As shown in Table 2 and FIG. 1, the inventive extract administered-group showed significant difference in glucose level from the control group after glucose was administered in 2 hours and thereby confirmed the glucose tolerance of the inventive extracts. Particularly, the effect of inventive extracts, the effect of decreasing the blood glucose level, was similar to that of metformin.

Experimental Example 3

Effect of *Elfvingia applanata* Extracts on Aldose Reductase Activity (1) Preparation of Aldose Reductase Crude aldose reductase was prepared as follows: rat lenses were removed from Sprague-Dawley rats weighing 250–280 g and frozen until use. The supernatant fraction of the rat lens homogenate was prepared according to the procedure described in the literature (Hayman & Kinoshita; *J. Biol. Chem.*, 240, pp877–882, 1965). Partially purified enzyme having its a specific activity of 6.5 U/mg was routinely used to test enzyme inhibition. The partially purified material was separated into 1.0 ml of aliquots and stored at −40° C.

(2) Measurement of Aldose Reductase Activity

Aldose reductase activities were assayed spectrophotometrically by measuring the decrease in absorption of NADPH at 340 nm over a 4 min period with DL-glyceraldehyde as a substrate according to the procedure described in the literature (Sato & Kador; *Biochem Pharmacol.*, 40(5), pp1033–42, 1990). Each 1.0 ml of cuvette containing equal units of enzyme, 0.1M sodium phosphate buffer (pH 6.2), 0.3 mM NADPH with or without 10 mM substrate and inhibitor was prepared. The concentration of inhibitors giving 50% inhibition of enzyme activity ($IC_{50}$) was calculated from the least-squares regression line of the logarithmic concentrations plotted against the remaining activity.

TABLE 3

Inhibitory effect of *Elfvingia applanata* extracts on rat lenses aldose reductase activity.

| Sample | Concentration (μg/ml) | Inhibition (%) | $IC_{50}$ (μg/ml) |
| --- | --- | --- | --- |
| TMG* | 10 | 76.4 | 0.46 (μM) |
|  | 1 | 51.3 |  |
|  | 0.1 | 40.6 |  |
| Epalrestat | 0.1 | 100 | 0.003 (μM) |
|  | 0.01 | 60.2 |  |
|  | 0.001 | 35.0 |  |
| Sample 1 | 100 | 100 | 1.67 |
|  | 10 | 80.3 |  |
|  | 1 | 39.8 |  |
| Sample 2 | 100 | 97.5 | 1.53 |
|  | 10 | 76.9 |  |
|  | 1 | 42.7 |  |
| Sample 3 | 100 | 98.5 | 8.73 |
|  | 10 | 56.5 |  |
|  | 1 | 3.6 |  |
| Sample 4 | 1000 | 100 | 17.57 |
|  | 100 | 88.0 |  |
|  | 10 | 35.3 |  |

Inhibition rate was calculated as percentage with respect to the control value.
TMG*: abbreviation of TetraMethylene Glutaric acid.

As can be seen from Table 3, the inventive extracts showed the inhibitory effect of aldose reductase in the dose-dependent manner.

Experimental Example 4

Inhibitory Effect of *Elfvingia applanata* Extracts on Sorbitol Accumulation in STZ-Induced Diabetes Mellitus Rats Among diabetes-induced rats prepared by described above, the animals showing higher serum glucose level than 600 mg/dl were selected, then epalrestat and *Elfvingia applanata* extracts were administered via an intragastric tube, once a day at a dose of 200 mg/kg/day for 2 weeks. The extract was suspended in saline containing 0.5% carboxymethyl cellulose. The animals were then sacrificed under ether anesthesia. The contents of sorbitol in the red blood cell, sciatic nerves, and lenses were determined enzymatically.

Enzymatic Measurement of Sorbitol

Sorbitol was measured by a modification of the enzymatic assay procedure described in the literature (Clements, R. S. et al.; *Science*, 166(908), pp1007–8, 1969).

0.5 ml of protein-free filtrate of tissues was added to a reaction mixture consisting of 1.0 ml of 0.05 M glycine buffer adjusted to pH 9.4 containing 0.2 mM nicotinamide adenine dinucleotide (NAD) and 0.64 U of sorbitol dehydrogenase. Blanks untreated with the filtrate, NAD, or sorbitol dehydrogenase, were routinely run simultaneously. The relative fluorescence due to NADH was measured with an excitation wavelength of 366 nm and an emission wavelength of 452 nm. Epalrestat used in the present invention is a conventional therapeutic drug for diabetic complications.

TABLE 4

The effect of *Elfvingia applanata* and epalrestat on the accumulation of sorbitol in the red blood cell of STZ-diabetic rats.

| Samples | Sorbitol (nmol/g Hg) | Inhibition (%) |
| --- | --- | --- |
| Normal | 63.2 ± 3.9 | — |
| Control | 403.6 ± 61.3 | — |
| Epalrestat | 108.7 ± 11.6** | 75.0 |
| Sample 1 | 277.8 ± 18.0* | 36.1 |
| Sample 2 | 201.9 ± 20.4* | 53.6 |
| Sample 3 | 138.1 ± 17.5** | 68.2 |
| Sample 4 | 222.7 ± 43.6* | 48.8 |

Significantly different from the control:
**$p < 0.01$,
*$p < 0.05$.

Figure 2:
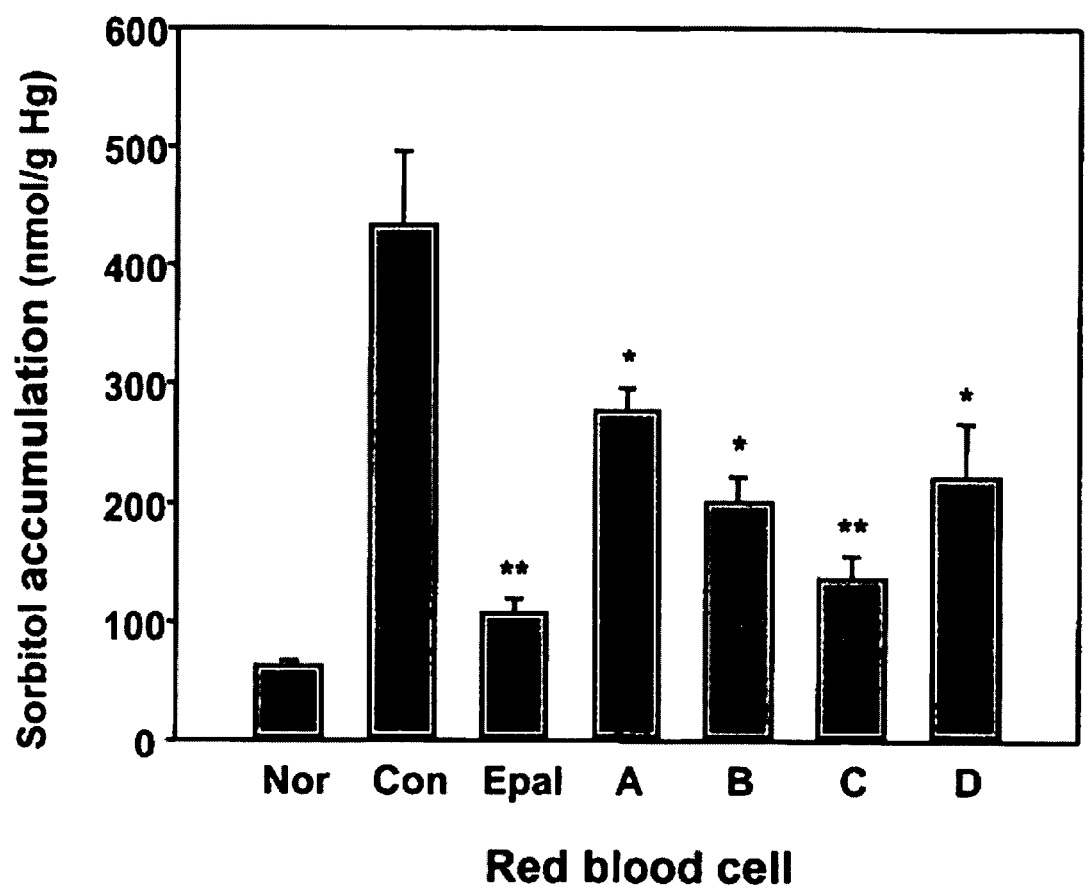
FIG. 2 shows the effect of *Elfvingia applanata* and epalrestat on the accumulation of sorbitol in the red blood cell of STZ-diabetic rats.

As shown in Table 4 and FIG. 2, the sorbitol level in the red blood cell of control STZ-diabetic rats was increased significantly comparing with that of normal group. Inventive water extract of brown part, sample 3, showed the significantly inhibiting effect of sorbitol increment. Moreover, the effect of inventive extracts, i.e., the decreasing effect of sorbitol level, was similar to that of epalrestat.

TABLE 5

The effect of *Elfvingia applanata* and epalrestat on the accumulation of sorbitol in the lenses of STZ-diabetic rats.

| Samples | Sorbitol (nmol/mg dry wt.) | Inhibition (%) |
| --- | --- | --- |
| Normal | 0.05 ± 0.02 | — |
| Control | 0.80 ± 0.04 | — |
| Epalrestat | 0.38 ± 0.05* | 52.5 |
| Sample 1 | 0.37 ± 0.07** | 53.8 |
| Sample 2 | 0.57 ± 0.07* | 28.8 |
| Sample 3 | 0.42 ± 0.08** | 47.5 |
| Sample 4 | 0.57 ± 0.10* | 28.8 |

Significantly different from the control:
**$p < 0.01$,
*$p < 0.05$

Figure 3:
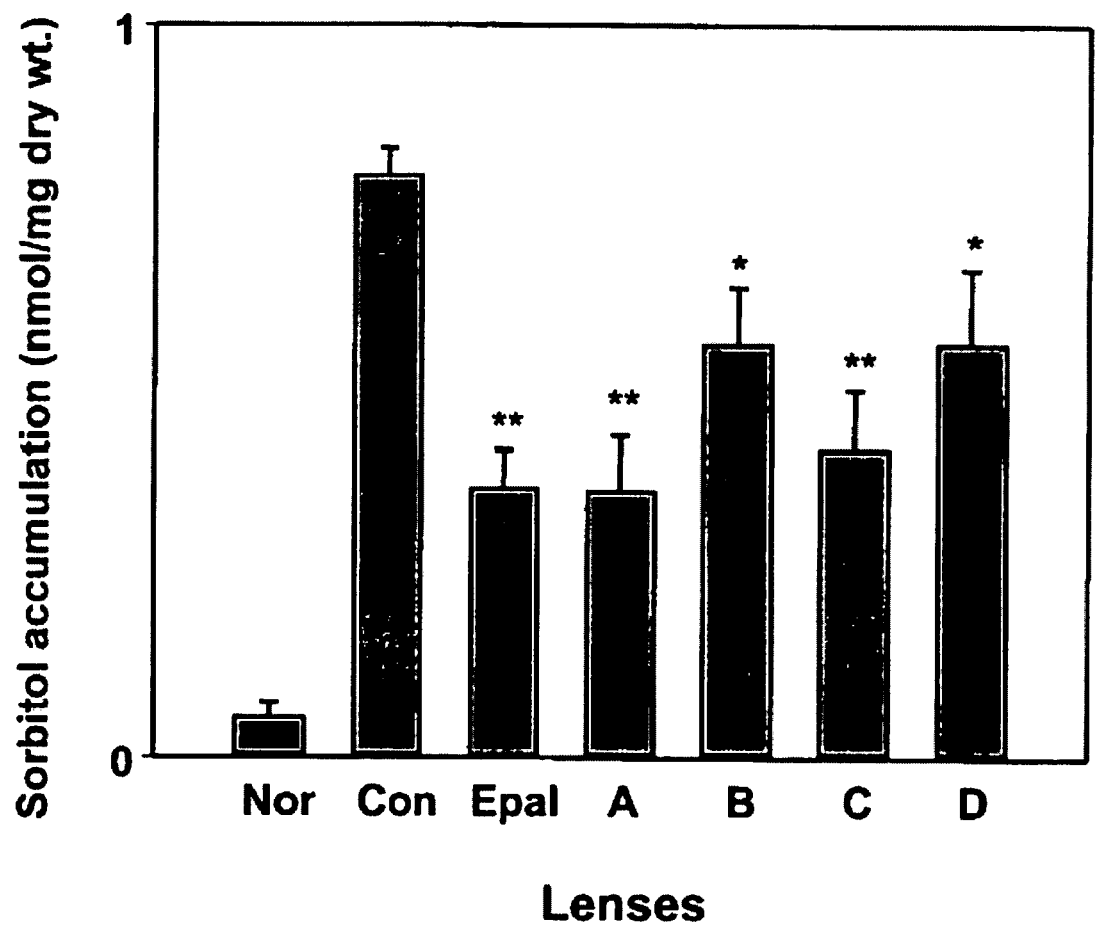
FIG. 3 presents the effect of *Elfvingia applanata* and epalrestat on the accumulation of sorbitol in the lenses of STZ-diabetic rats.

As shown in Table 5 and FIG. 3, the sorbitol level in the lenses of control STZ-diabetic rats was increased significantly comparing with that of normal group. Inventive water extract of brown part showed the significantly inhibiting effect of sorbitol increment. Moreover, the effect of inventive extracts, i.e., the decreasing effect of sorbitol level, was similar to that of epalrestat.

TABLE 6

The effect of *Elfvingia applanata* and epalrestat on the accumulation of sorbitol in the sciatic nerves of STZ-diabetic rats.

| Samples | Sorbitol (nmol/mg dry wt.) | Inhibition (%) |
| --- | --- | --- |
| Normal | 2.0 ± 0.3 | — |
| Control | 10.4 ± 1.4 | — |
| Epalrestat | 4.3 ± 0.5** | 58.2 |
| Sample 1 | 4.9 ± 0.7** | 52.4 |
| Sample 2 | 5.0 ± 0.7** | 52.0 |
| Sample 3 | 6.7 ± 0.6* | 35.8 |
| Sample 4 | 6.1 ± 0.4* | 40.9 |

Significantly different from the control:
**$p < 0.01$,
*$p < 0.05$.

Figure 4:
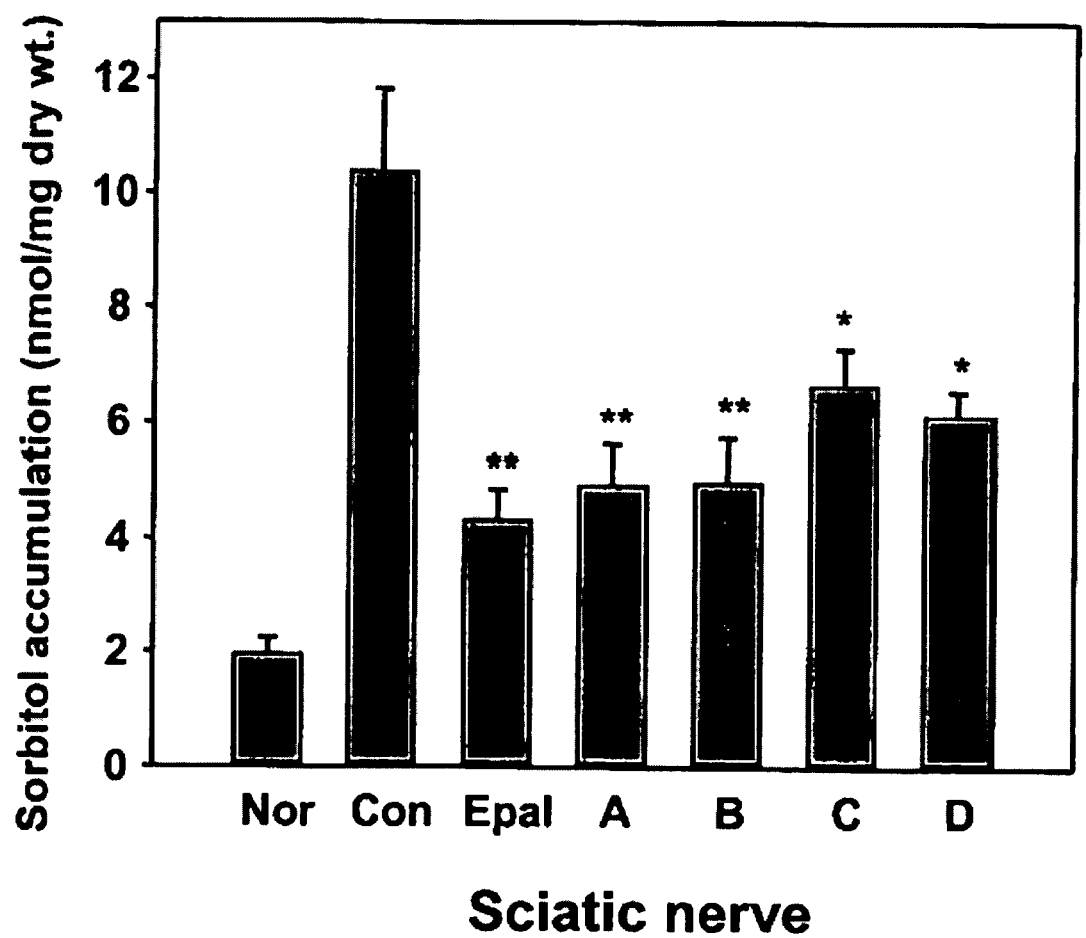
FIG. 4 shows the effect of *Elfvingia applanata* and epalrestat on the accumulation of sorbitol in the sciatic nerve of STZ-diabetic rats.

As shown in Table 6 and FIG. 4, the sorbitol level in the sciatic nerves of control STZ-diabetic rats was increased significantly comparing with that of normal group. Inventive methanol extract showed the significantly inhibiting effect of sorbitol increment, similar to that of the epalrestat.

What is claimed is:

1. A method for preparing an extract of *Elfvingia applanata* KARST comprising the steps of: dividing *Elfvingia applanata* KARST into a brown part and a white part; pulverizing said white part to a powder; adding 1 to 10-fold volume of methanol to the powder to obtain a mixture; heating the mixture at a temperature ranging from 60 to 90° C. for a period ranging from 1 to 24 hours to obtain a white powder extract; concentrating the extract under reduced pressure and lyophilizing to obtain said extract.

2. A pharmaceutical composition for the treatment of diabetic complications caused by increased aldose reductase and sorbitol accumulation comprising a therapeutically effective amount of an extract of *Elfvingia applanata* KARST and a pharmaceutically acceptable carrier, whereby the extract is prepared by the method according to claim 1.

* * * * *